United States Patent [19]

Iwanami et al.

[11] 4,165,429
[45] Aug. 21, 1979

[54] 7α-METHOXY-CEPHALOSPORANIC ACID DERIVATIVES

[75] Inventors: Masaru Iwanami, Yokohama; Masuo Murakami, Tokyo; Yoshinobu Nagano, Niiza; Masaharu Fujimoto, Tokyo; Tetsuya Maeda, Urawa; Noriaki Nagano, Ages; Atsuki Yamazaki, Ichikawa, all of Japan

[73] Assignee: Yamanouchi Pharmaceutical Co., Ltd., Tokyo, Japan

[21] Appl. No.: 806,932

[22] Filed: Jun. 15, 1977

[30] Foreign Application Priority Data

| Jun. 28, 1976 | [JP] | Japan | 51-76209 |
| Jul. 7, 1976 | [JP] | Japan | 51-80659 |
| Oct. 8, 1976 | [JP] | Japan | 51-121143 |
| Oct. 15, 1976 | [JP] | Japan | 51-123601 |
| Dec. 27, 1976 | [JP] | Japan | 51-159908 |
| Mar. 11, 1977 | [JP] | Japan | 52-26835 |

[51] Int. Cl.$^2$ .................. C07D 501/56; A61K 31/545
[52] U.S. Cl. ....................... 544/21; 424/246
[58] Field of Search ......................... 544/21

[56] References Cited

U.S. PATENT DOCUMENTS

| 3,516,997 | 6/1970 | Takano et al. | 544/26 |
| 3,819,623 | 6/1974 | Takano et al. | 544/26 |
| 3,887,549 | 6/1975 | Christensen | 544/21 X |
| 3,984,403 | 10/1976 | Fujisawa et al. | 544/21 X |
| 4,007,177 | 2/1977 | Nakao et al. | 544/21 |
| 4,017,488 | 4/1977 | Hiraoka et al. | 544/21 |
| 4,051,129 | 9/1977 | Shimizu et al. | 544/21 |

FOREIGN PATENT DOCUMENTS

| 2432415 | 1/1975 | Fed. Rep. of Germany | 544/21 |
| 2440790 | 3/1975 | Fed. Rep. of Germany | 544/21 |
| 2445341 | 4/1975 | Fed. Rep. of Germany | 544/21 |
| 2412598 | 5/1975 | Fed. Rep. of Germany | 544/21 |
| 2455884 | 5/1975 | Fed. Rep. of Germany | 544/21 |
| 2448582 | 6/1975 | Fed. Rep. of Germany | 544/21 |
| 51-52195 | 5/1976 | Japan | 544/21 |
| 7216268 | 6/1973 | Netherlands | 544/21 |
| 1412886 | 11/1975 | United Kingdom | 544/21 |

*Primary Examiner*—Donald G. Daus
*Assistant Examiner*—Diana G. Rivers
*Attorney, Agent, or Firm*—Burgess, Ryan and Wayne

[57] ABSTRACT

Novel 7α-methoxy-7β-heterocyclic thioacetamido-3-heterocyclic thiomethyl-Δ$^3$-cephem-4-carboxylic acid derivatives and pharmaceutically acceptable salts thereof. These compounds show high antibiotic activities against various microorganisms including gram positive and negative bacteria.

3 Claims, No Drawings

7α-METHOXY-CEPHALOSPORANIC ACID DERIVATIVES

BACKGROUND OF THE INVENTION

1. Field of the Invention

The present invention relates to cephalosporins having a methoxy group at the 7α-position and also to processes of producing the cephalosporins. More particularly, the invention relates to 7α-methoxy-7β-heterocyclic thioacetamido-3-heterocyclic thiomethyl-Δ³-cephem-4-carboxylic acid represented by the general formula

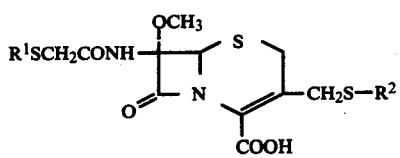

wherein R¹ represents

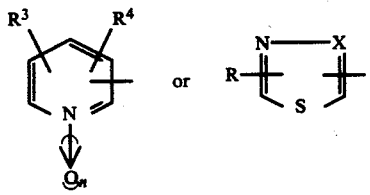

(wherein R³ and R⁴, which may be the same or different, each represents a hydrogen atom, a hydroxy group, an amino group or a lower alkyl group; n represents 0 or 1; R⁵ represents a hydroxy group, an amino group, a mercapto group, a lower alkylamino group, a lower alkanoylamino group, a lower alkoxycarbonylamino group, a carboxy lower alkylthio group, or a 3-lower alkylureido group; and X represents —CH= or —N=) and R² represents a 5-lower alkyl-1,3,4-thiadiazol-2-yl group or a 1-lower alkyltetrazol-5-yl group, and the pharmaceutically acceptable salts thereof.

2. Description of the Prior Art

Cephalosporin derivatives having a methoxy group at the 7α-position, a heterocyclic acyl group at the 7β-position, and a heterocyclic thiomethyl group at the 3-position are known. For example, U.S. Pat. Nos. 4,017,488 and 4,051,129 discloses 7α-methoxy-7β-(5-methyl-substituted or unsubstituted)-1,3,4-thiadiazol-2-yl-thioacetamido-3-(1-methyltetrazol-5-yl)-thiomethyl-Δ³-cephem-4-carboxylic acid. Furthermore, Japanese Patent Application Laid Open No. 52,195/'76 discloses 7β-(2-amino-4-thiazolyl)acetamido-7α-methoxy-3-(1-methyltetrazol-5-yl)thiomethyl-Δ³-cephem-4-carboxylic acid. Other similar compounds are also described in, for example, U.S. Pat. No. 3,887,549; Dutch Pat. No. 7,216,268; German Offenlegungsschriften Nos. 2,440,790, 2,448,582, 2,445,341, and 2,455,884 and British Pat. No. 1,412,886.

SUMMARY OF THE INVENTION

An object of this invention is to provide novel cephalosporin derivatives having excellent antibiotic activity against gram positive and negative bacteria.

It has now been found that the aforesaid object of this invention can be attained by the provision of 7α-methoxy-7β-heterocyclic thioacetamido-3-heterocyclic thiomethyl-Δ³-cephem-4-carboxylic acid shown by the aforesaid general formula I and the pharmaceutically acceptable salts thereof.

The compounds of this invention are suggested as very broad and vague concepts such as 5-membered or 6-membered heterocyclic ring-substituted cephalosporin derivatives in the known art but have neither been prepared nor been investigated for pharmaceutical activity prior to the inventors' discovery.

DETAILED DESCRIPTION OF THE INVENTION

Now, in the compounds of this invention represented by formula I, examples of the lower alkyl group include straight chain or branched chain hydrocarbon groups having 1–4 carbon atoms, such as, methyl group, ethyl group, propyl group, isopropyl group, n-butyl group, sec-butyl group, tert-butyl group, etc. Also, as the pharmaceutically acceptable salts of the aforesaid compounds of this invention, there are the alkali metal salts such as sodium salts, potassium salts, etc.; the alkaline earth metal salts such as calcium salts, magnesium salts, etc.; the organic amine salts such as trimethylamine salts, ethanolamine salts, diethanolamine salts, lysine salts, alginine salts, ornithine salts, etc.

In cases where the substituents mean hydroxy group, mercapto group or amino group, it is possible for the substituents to exist in more than one tautomeric form, i.e. the hydroxy or oxo, mercapto or thioxo and substituted or unsubstituted amino or substituted or unsubstituted imino group. The compounds may exist exclusively as one tautomer or may be in equilibrium mixture between other forms.

The compounds of this invention may be produced by several modes of reaction which vary with the selection of the starting materials, the availability of reaction reagents, the separation procedure of by-products of the reaction, the applicability of reaction conditions, etc. The typical reaction modes of producing the aimed compounds of this invention will be illustrated below but not to limit it in any way.

In the first reaction mode, 7α-methoxy-3-heterocyclic thiomethyl-7-substituted or unsubstituted amino-Δ³-cephem-4-carboxylic acid represented by the general formula

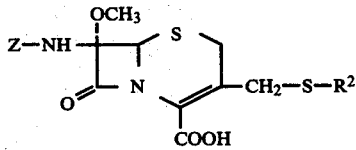

wherein Z represents the Y—CH₂CO— group (wherein Y represents a halogen atom) or a hydrogen atom and R² represents 5-lower alkyl-1,3,4-thiadiazol-2-yl group or 1-lower alkyl-tetrazol-5-yl group, is made to react with the heterocyclic ring compound represented by the general formula

R¹—S—B wherein R¹ represents

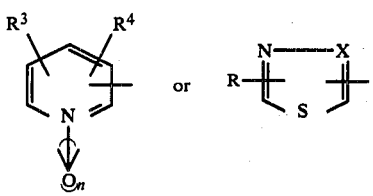

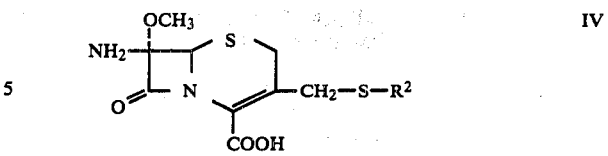

(wherein $R^3$ and $R^4$, which may be the same or different, each represents a hydrogen atom, a hydroxy group, an amino group, or a loweralkyl group; n represents 0 or 1; $R^5$ represents a hydroxy group, an amino group, a mercapto group, a lower alkylamino group, a lower alkanoylamino group, a lower alkoxycarbonylamino group, a carboxy lower alkylthio group, or a 3-lower alkylureido group; and X represents —CH= or =N—) and B represents a hydrogen atom or $R^1$—S— when Z is Y—$CH_2CO$— group or represents —$CH_2COOH$ or the reactive derivative of the carboxy group thereof when Z is a hydrogen atom.

The reaction of the first mode is explained below in more detail.

In one type of the first mode of reaction, 7β-haloacetamido-7α-methoxy-3-heterocyclic thiomethyl-$\Delta^3$-cephem-4-carboxylic acid represented by the general formula

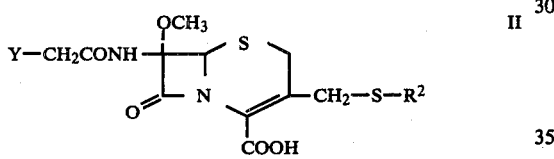

wherein Y and $R^2$ have the same meaning as above, is caused to react with the compound shown by
$R^1$—S—A   III (wherein A represents a hydrogen atom or $R^1$-S—) in the presence of a base.

That is, the reaction of compound of formula II and the compound of formula III is usually performed in an organic solvent which does not affect the reaction, water, or a mixture thereof under cooling or at room temperature. As the base used in this reaction, there are aliphatic nitrogen bases, aromatic nitrogen bases, heterocyclic nitrogen bases, alkali metal carbonates, alkali metal hydrogencarbonates, etc. Suitable examples of these bases are triethylamine, N,N-dimethylaniline, N-ethylmorpholine, pyridine, collidine, 2,6-lutidine, potassium carbonate, sodium carbonate, potassium hydrogencarbonate, and sodium hydrogencarbonate.

As the halogen atom shown by Y in the above-described formula II, there are the chlorine atom, bromine atom, fluorine atom, etc. The amount of the compound of formula III used in this reaction is equimolar amount or excessive molar amount to that of compound of formula II, preferably 1-2 mole times.

Typical examples of the organic solvent which is used without influence on the reaction are methanol, chloroform, methylene chloride, ethylene chloride, acetone, tetrahydrofuran, dimethylformamide, etc.

In the othertype of the first reaction mode, 7β-amino-7α-methoxy-3-heterocyclic thiomethyl-$\Delta^3$-cephem-4-carboxylic acid represented by the formula

wherein $R^2$ has the same meaning as above, is allowed to react with an equimolar or excessive molar amount, preferably 1-2 mole times of the heterocyclic thioacetic acid shown by $R^1SCH_2COOH$   V wherein $R^1$ has the same meaning as above, or the reactive derivative of the carboxy group thereof in an organic solvent which does not effect the reaction.

When the carboxy group of the compound of formula V is not protected, the reaction is carried out in the presence of a condensing agent such as dicyclohexylcarbodiimide, carbonyldiimidazole, etc. Also, when the reactive derivative of the carboxy group is an acid halide such as acid chloride, etc., the reaction is performed in the presence of an almost equimolar amount of a base such as triethylamine, pyridine, etc. Furthermore, as the reactive derivative of the carboxy group, active esters such as p-nitrophenyl ester, etc., may be employed.

In the second reaction mode of producing the aimed compounds of this invention, 7α-methoxy-7β-heterocyclicthioacetamido-3-acetoxymethyl-$\Delta^3$-cephem-4-carboxylic acid represented by the general formula

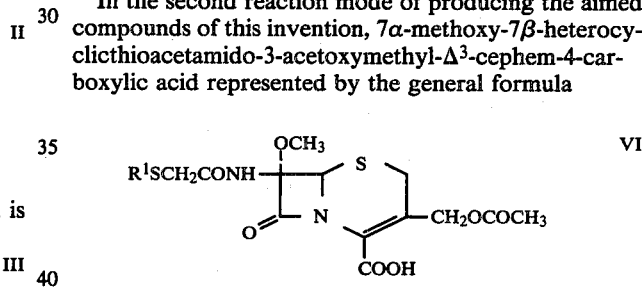

wherein $R^1$ has the same meaning as above, is caused to react with the compound shown by $R^2$—SM   VII wherein $R^2$ has the same meaning as above and M represents a hydrogen atom or an alkali metal atom.

It is preferred to conduct the reaction under nearly neutral conditions and the compound of formula VI is made to react with an equimolar amount or molar excess of the compound of formula VII. As the alkali metal salt of the compound of formula VII, there are the sodium salt, potassium salt, etc. When the compound of formula VII wherein M is a hydrogen atom is used, it is preferred to perform the reaction in the presence of a base such as an alkali hydroxide, an alkali metal carbonate, an alkali metal hydrogencarbonate, a trialkylamine (e.g. triethylamine), pyridine, dimethylaniline, etc. The reaction is usually performed in an organic solvent, which does not affect the reaction, such as acetone, dimethylformamide, methanol, ethanol, etc., water, or a mixture thereof, or further a phosphate buffer solution at room temperature or under heating.

The carboxy group of at 3-position of the cephem ring of the starting material may also be protected by a known protecting group such as the diphenyl methyl group, triphenyl methyl group, methyl group or ethyl group during the reaction steps and can be split in the final stage by a procedure known in the art.

The compounds of this invention thus produced can be converted into the nontoxic pharmaceutically acceptable or useful salts thereof. These salts may be formed in an ordinary manner. For example, the alkali metal salt of the compound of formula I can be obtained by adding to the compound an n-butanol solution of an alkali metal 2-ethylhexanoate and then adding an organic solvent having low solubility of the formed salt, such as ether, ethyl acetate, etc. Also, by adding to the compound an equimolar or a slightly excessive amount of an organic base such as triethylamine, diethanolamine, alginine, lysine, etc., the salt of the organic base can be formed. Or, further, by adding to the compound aqueous ammonia or an organic solvent solution of ammonia, the ammonium salt of the compound can also be formed. These salts are interchangeable with each other in an ordinary manner, if desired.

The compound of the formula I or the salt thereof of this invention is isolated and purified in an ordinary manner.

The compounds of this invention produced by the aforesaid methods are antibiotics showing excellent antimicrobial activity against various gram positive and negative bacteria and are useful for treatment and prophylaxis of various diseases caused by these bacteria, for preservatives of foods and chemical industrial products, and as additives for feed. The minimum inhibiting concentrations (MIC) (mcg/ml) thereof by an in vitro test are shown in the following tables in detail.

Table I

| | Ex. No. | | | | | |
|---|---|---|---|---|---|---|
| | 1 | 2 | 3 | 4 | 5 | 6 |
| B. megatherium 10778 | 3.13 | 6.25 | 6.25 | 3.13 | 6.25 | 3.13 |
| B. subtilis ATCC 6633 | 0.78 | 0.78 | 0.78 | 0.78 | 3.13 | 0.78 |
| Micrococcus flavas ATCC 10240 | 0.19 | 0.19 | 0.19 | 0.78 | 0.39 | 0.19 |
| Sarcina lutea ATCC 9341 | 0.09 | 0.09 | 0.09 | 0.19 | 0.39 | 0.19 |
| Staph. aureus ATCC 6538P | 0.78 | 0.39 | 0.78 | 1.56 | 1.56 | 0.78 |
| Staph. aureus Smith | 1.56 | 0.78 | 3.13 | 3.13 | 6.25 | 1.56 |
| Staph. aureus Terashima | 1.56 | 0.78 | 1.56 | 3.13 | 3.13 | 0.78 |
| Corynebacterium xerosis | 0.78 | 0.78 | 0.78 | 1.56 | 3.13 | 0.78 |
| Mycobacterium 607 | 6.25 | 12.5 | 50 | 50 | 12.5 | 3.13 |
| Mycobacterium phlei | 6.25 | 12.5 | 50 | 12.5 | 12.5 | 3.13 |
| Staph. aureus Oonuma (JM.LM.EM.SPM.OLM.SM.PC.SA-R) | 1.56 | 0.78 | 3.13 | 3.13 | 6.25 | 1.56 |
| E. coli Kauffmann 0-1 | 0.39 | 1.56 | 6.25 | 1.56 | 0.78 | 0.78 |
| E. coli NIHJ | 0.39 | 0.78 | 3.13 | 0.78 | 0.78 | 0.78 |
| E. coli alkalescens I 011628 | 0.39 | 1.56 | 3.13 | 1.56 | 0.78 | 0.78 |
| Kleb. pneumoniae ATCC 10031 | 0.39 | 0.78 | 0.78 | 0.78 | 0.39 | 0.78 |
| Vibrio Hy 133 | 0.78 | 0.39 | 0.78 | 1.56 | 0.78 | 1.56 |
| Sal. cholerae-suis 1348 | 0.78 | 6.25 | 25 | 6.25 | 0.78 | 0.78 |
| Sal. typhi H901W | 0.39 | 0.39 | 0.78 | 1.56 | 0.78 | 0.39 |
| Sal. euteritidis 1891 | 0.19 | 0.19 | 0.78 | 0.78 | 0.39 | 0.39 |
| Shigella flexneri 2a 1675 | 0.78 | 6.25 | 25 | 3.13 | 0.78 | 1.56 |
| Shigella sonnei II 37148 | 0.78 | 3.13 | 25 | 6.25 | 0.78 | 0.78 |
| Prot. vulgaris OXK US | 0.78 | 0.78 | 1.56 | 1.56 | 3.13 | 1.56 |
| Prot. mirabilis IFM OM-9 | 1.56 | 3.13 | 25 | 6.25 | 6.25 | 3.13 |

| | 7 | 8 | 9 | 10 | 11 | 12 |
|---|---|---|---|---|---|---|
| B. megatherium 10778 | 6.25 | 12.5 | 3.13 | 6.25 | 6.25 | 3.13 |
| B. subtilis ATCC 6633 | 3.13 | 6.25 | 3.13 | 1.56 | 3.13 | 1.56 |
| Micrococcus flavas ATCC 10240 | 0.39 | 0.39 | 0.19 | 0.09 | 0.39 | 0.04 |
| Sarcina lutea ATCC 9341 | 0.39 | 0.39 | 0.39 | 0.09 | 0.39 | 0.04 |
| Staph. aureus ATCC 6538P | 1.56 | 1.56 | 1.56 | 0.78 | 1.56 | 0.78 |
| Staph. aureus Smith | 3.13 | 6.25 | 3.13 | 1.56 | 3.13 | 1.56 |
| Staph. aureus Terashima | 3.13 | 3.13 | 3.13 | 1.56 | 3.13 | 1.56 |
| Corynebacterium xerosis | 3.13 | 6.25 | 3.13 | 1.56 | 3.13 | 1.56 |
| Mycobacterium 607 | 12.5 | 12.5 | 6.25 | 3.13 | 12.5 | 3.13 |
| Mycobacterium phlei | 12.5 | 12.5 | 6.25 | 3.13 | 12.5 | 3.13 |
| Staph. aureus Oonuma (JM.LM.EM.SPM.OLM.SM.PC.SA-R) | 3.13 | 6.25 | 3.13 | 3.13 | 3.13 | 1.56 |
| E. coli Kauffmann 0-1 | 1.56 | 3.13 | 0.78 | 3.13 | 1.56 | 1.56 |
| E. coli NIHJ | 0.78 | 3.13 | 0.78 | 0.78 | 0.78 | 0.78 |
| E. coli alkalescens I 011628 | 0.78 | 3.13 | 0.78 | 3.13 | 1.56 | 1.56 |
| Kleb. pneumoniae ATCC 10031 | 0.78 | 3.13 | 0.78 | 0.19 | 0.78 | 0.39 |
| Vibrio Hy 133 | 3.13 | 3.13 | 1.56 | 1.56 | 1.56 | 1.56 |
| Sal. cholerae-suis 1348 | 1.56 | 6.25 | 0.39 | 6.25 | 0.39 | 1.56 |
| Sal. typhi H901W | 0.78 | 1.56 | 0.78 | 0.19 | 0.78 | 0.78 |
| Sal. euteritidis 1891 | 0.39 | 0.78 | 0.19 | 0.09 | 0.39 | 0.39 |
| Shigella flexneri 2a 1675 | 3.13 | 12.5 | 0.78 | 3.13 | 3.13 | 3.13 |
| Shigella sonnei II 37148 | 3.13 | 6.25 | 0.78 | 6.25 | 3.13 | 3.13 |
| Prot. vulgaris OXK US | 1.56 | 3.13 | 0.78 | 0.39 | 0.78 | 1.56 |
| Prot. mirabilis IFM OM-9 | 6.25 | 6.25 | 1.56 | 1.56 | 3.13 | 3.13 |

| | 13 | 14 | 15 | 16 | 17 | 18 |
|---|---|---|---|---|---|---|
| B. megatherium 10778 | 6.25 | 6.25 | 3.13 | 6.25 | 3.13 | 3.13 |
| B. subtilis ATCC 6633 | 1.56 | 1.56 | 1.56 | 3.13 | 1.56 | 3.13 |
| Micrococcus flavas | 0.39 | 0.09 | 0.19 | 0.39 | 0.09 | 0.19 |

Table I-continued

| | \multicolumn{6}{c}{Ex. No.} | | | | | |
|---|---|---|---|---|---|---|
| ATCC 10240 | | | | | | |
| *Sarcina lutea* ATCC 9341 | 0.39 | 0.04 | 0.09 | 0.19 | 0.09 | 0.19 |
| *Staph. aureus* ATCC 6538P | 1.56 | 0.78 | 0.78 | 1.56 | 1.56 | 1.56 |
| *Staph. aureus* Smith | 3.13 | 1.56 | 3.13 | 3.13 | 3.13 | 3.13 |
| *Staph. aureus* Terashima | 3.13 | 1.56 | 1.56 | 3.13 | 3.13 | 3.13 |
| *Corynebacterius xerosis* | 1.56 | 1.56 | 1.56 | 1.56 | 3.13 | 3.13 |
| *Mycobacterium* 607 | 50 | 3.13 | 6.25 | 6.25 | 50 | 12.5 |
| *Mycobacterium phlei* | 25 | 3.13 | 3.13 | 6.25 | 25 | 6.25 |
| *Staph. aureus* Oonuma (JM. LM.EM.SPM.OLM.SM. PC.SA-R) | 3.13 | 1.56 | 1.56 | 3.13 | 3.13 | 3.13 |
| *E. coli* Kauffmann 0–1 | 12.5 | 6.25 | 3.13 | 3.13 | 3.13 | 0.78 |
| *E. coli* NIHJ | 3.13 | 1.56 | 0.78 | 0.78 | 1.56 | 0.78 |
| *E. coli alkalescens* I 011628 | 6.25 | 3.13 | 1.56 | 3.13 | 3.13 | 0.78 |
| *Kleb. pneumoniae* ATCC 10031 | 1.56 | 0.39 | 0.39 | 0.78 | 1.56 | 0.78 |
| *Vibrio* Hy 133 | 3.13 | 1.56 | 1.56 | 3.13 | 3.13 | 3.13 |
| *Sal. cholerae-suis* 1348 | 12.5 | 12.5 | 6.25 | 6.25 | 1.56 | 0.78 |
| *Sal. typhi* H901W | 3.13 | 0.39 | 0.39 | 0.78 | 1.56 | 0.78 |
| *Sal. euteritidis* 1891 | 0.78 | 0.09 | 0.19 | 0.39 | 0.39 | 0.19 |
| *Shigella flexneri* 2a 1675 | 25 | 6.25 | 6.25 | 6.25 | 6.25 | 1.56 |
| *Shigella sonnei* II 37148 | 25 | 12.5 | 6.25 | 6.25 | 6.25 | 3.13 |
| *Prot. vulgaris* OXK US | 3.13 | 0.78 | 0.39 | 1.56 | 0.78 | 0.78 |
| *Prot. mirabilis* IFM OM-9 | 12.5 | 3.13 | 1.56 | 6.25 | 3.13 | 1.56 |

| | 19 | 20 | 21 | 22 | 24 | 24 |
|---|---|---|---|---|---|---|
| *B. megatherium* 10778 | 3.13 | 3.13 | 3.13 | 6.25 | 1.56 | 6.25 |
| *Micrococcus flavas* ATCC 10240 | 0.19 | 0.09 | 0.19 | 0.19 | 0.10 | 0.39 |
| *Sarcina lutea* ATCC 9341 | 0.09 | <0.04 | <0.04 | 0.09 | <0.05 | 0.20 |
| *Staph. aureus* ATCC 6538P | 1.56 | 0.39 | 0.39 | 0.39 | 0.39 | 1.56 |
| *Staph. aureus* Smith | 3.13 | 0.78 | 0.78 | 1.56 | 0.78 | 6.25 |
| *Staph. aureus* Terahima | 1.56 | 0.78 | 0.78 | 0.78 | 0.39 | 3.13 |
| *Corynebacterium xerosis* | 1.56 | 0.78 | 0.78 | 0.78 | 0.20 | 1.56 |
| Mycobacterium 607 | 6.25 | 3.13 | 6.25 | 12.5 | 1.56 | 6.25 |
| *Mycobacterium phlei* | 3.13 | 3.13 | 6.25 | 12.5 | 1.56 | 6.25 |
| *Staph. aureus* Oonuma (JM. LM.EM.SPM.OLM.SM. PC.SA-R) | 3.13 | 0.78 | 0.78 | 1.56 | 0.78 | 6.25 |
| *E. coli* Kauffmann 0–1 | 1.56 | 1.56 | 1.56 | 1.56 | 0.39 | 3.13 |
| *E. coli* NIHJ | 0.39 | 0.39 | 0.39 | 0.78 | 0.39 | 1.56 |
| *E. coli alkalescens* I 011628 | 1.56 | 0.78 | 0.78 | 1.56 | 0.20 | 1.56 |
| *Kleb. pneumoniae* ATCC 10031 | 0.19 | 0.19 | 0.19 | 0.39 | 0.20 | 1.56 |
| *Vibrio* Hy 133 | 3.13 | 0.78 | 0.39 | 0.78 | 0.39 | 1.56 |
| *Sal. cholerae-suis* 1348 | 6.25 | 3.13 | 1.56 | 3.13 | 0.78 | 3.13 |
| *Sal. typhi* H901W | 0.19 | 0.39 | 0.19 | 0.78 | 0.20 | 1.56 |
| *Sal. euteritidis* 1891 | 0.09 | 0.19 | 0.19 | 0.39 | 0.10 | 0.78 |
| *Shigella flexneri* 2a 1675 | 1.56 | 0.78 | 0.78 | 3.13 | 0.39 | 6.25 |
| *Shigella sonnei* II 37148 | 6.25 | 1.56 | 1.56 | 3.13 | 0.39 | 3.13 |
| *Prot. vulgaris* OXK US | 0.39 | 0.78 | 0.78 | 1.56 | 0.78 | 6.25 |
| *Prot. mirabilis* IFM OM-9 | 0.78 | 1.56 | 1.56 | 3.13 | 0.78 | 6.25 |

| | 25 | CEZ |
|---|---|---|
| *B. megatherium* 10778 | 3.13 | 0.39 |
| *B. subtilis* ATCC 6633 | 6.25 | 0.19 |
| *Micrococcus flavas* ATCC 10240 | 0.19 | 0.19 |
| *Sarcina lutea* ATCC 9341 | 0.39 | 0.19 |
| *Staph. aureus* ATCC 6538P | 1.56 | 0.19 |
| *Staph. aureus* Smith | 3.13 | 1.56 |
| *Staph. aureus* Terashima | 3.13 | 0.78 |
| *Corynebacterium xerosis* | 3.13 | 0.19 |
| Mycobacterium 607 | 6.25 | >100 |
| *Mycobacterium phlei* | 6.25 | >100 |
| *Staph. aureus* Oonuma (JM. LM.EM.SPM.OLM.SM. PC.SA-R) | 3.13 | 1.56 |
| *E. coli* Kauffmann 0–1 | 25 | 1.56 |
| *E. coli* NIHJ | 3.13 | 3.13 |
| *E. coli alkalescens* I 011628 | 12.5 | 3.13 |
| *Kleb. pneumoniae* ATCC 10031 | 1.56 | 1.56 |
| *Vibrio* Hy 133 | 1.56 | 0.78 |
| *Sal. cholerae-suis* 1348 | 25 | 1.56 |
| *Sal. typhi* H901W | 0.78 | 1.56 |
| *Sal. euteritidis* 1891 | 0.78 | 1.56 |
| *Shigella flexneri* 2a 1675 | 50 | 1.56 |
| *Shigella sonnei* II 37148 | 50 | 1.56 |
| *Prot. vulgaris* OXK US | 3.13 | 3.13 |

Table I-continued

| | Ex. No. | |
|---|---|---|
| Prot. mirabilis IFM OM-9 | 6.25 | 6.25 |

(CEZ: Cefazolin) Cefazolin)

Table 2

| | Ex. No. | | | | |
|---|---|---|---|---|---|
| | 1 | 2 | 3 | 4 | 5 |
| Staph. aureus 209P | 0.78 | 0.78 | 1.56 | 1.56 | 1.56 |
| E. coli NIHJ | 0.39 | 0.78 | 1.56 | 1.56 | 1.56 |
| E. coli Ebara | 0.78 | 6.25 | 25 | 6.25 | 1.56 |
| E. coli Takeda | 1.56 | 12.5 | 50 | 25 | 1.56 |
| Ent. cloacae | 0.78 | 0.39 | 0.78 | 1.56 | 1.56 |
| Ent. cloacae V-8 | 100 | >100 | >100 | >100 | 100 |
| Ent. aerogenes | 0.78 | 0.39 | 25 | 1.56 | 1.56 |
| Ent. aerogenes NY-2 | >100 | >100 | 50 | >100 | >100 |
| Kleb. pneumoniae Y-11 | 3.13 | 3.13 | 12.5 | 3.13 | 0.78 |
| Kleb. pneumoniae V-17 | 0.78 | 3.13 | 100 | 6.25 | 1.56 |
| Serratia marcescens | 50 | 100 | >100 | >100 | 6.25 |
| Serratia marcescens No. 10 | 25 | 100 | >100 | >100 | 12.5 |
| Prot. morganii Kono | 25 | 100 | >100 | 100 | 12.5 |
| Prot. rettgeri Y-1 | >100 | >100 | >100 | >100 | 25 |
| Citrobacter freundii | 25 | 100 | >100 | >100 | 100 |
| Pseud. pyocyanea NCTC 10490 | >100 | >100 | >100 | >100 | >100 |

| | 6 | 7 | 8 | 9 | 10 |
|---|---|---|---|---|---|
| Staph. aureus 209P | 1.56 | 3.13 | 3.13 | 1.56 | 0.78 |
| E. coli NIHJ | 1.56 | 1.56 | 1.56 | 1.56 | 0.78 |
| E. coli Ebara | 1.56 | 6.25 | 6.25 | 1.56 | 6.25 |
| E. coli Takeda | 6.25 | 100 | 12.5 | 3.13 | 25 |
| Ent. cloacae | 3.13 | 3.13 | 6.25 | 3.13 | 1.56 |
| Ent. cloacae V-8 | >100 | >100 | >100 | 100 | >100 |
| Ent. aerogenes | 3.13 | 3.13 | 6.25 | 3.13 | 1.56 |
| Ent. aerogenes NY-2 | >100 | >100 | >100 | >100 | >100 |
| Kleb. pneumoniae Y-11 | 1.56 | 3.13 | 3.13 | 0.78 | 6.25 |
| Kleb. pneumoniae V-17 | 1.56 | 3.13 | 6.25 | 0.78 | 6.25 |
| Serratia marcesceus | 100 | 50 | 100 | 50 | 50 |
| Serratia marcesceus No. 10 | 50 | 50 | 100 | 50 | 50 |
| Prot. morganii Kono | 25 | 50 | >100 | 25 | 25 |
| Prot. rettgeri Y-1 | >100 | >100 | >100 | 100 | >100 |
| Citrobacter freundii | 25 | 100 | 50 | 50 | 25 |
| Pseud pyocyanea NCTC 10490 | >100 | >100 | >100 | >100 | >100 |

| | 11 | 12 | 13 | 14 | 15 |
|---|---|---|---|---|---|
| Staph. aureus 209P | 1.56 | 1.56 | 1.56 | 1.56 | 1.56 |
| E. coli NIHJ | 0.78 | 0.78 | 1.56 | 3.13 | 1.56 |
| E. coli Ebara | 1.56 | 3.13 | 12.5 | 12.5 | 3.13 |
| E. coli Takeda | 6.25 | 25 | 50 | 50 | 25 |
| Ent. cloacae | 3.13 | 1.56 | 3.13 | 1.56 | 1.56 |
| Ent. cloacae V-8 | >100 | >100 | >100 | >100 | >100 |
| Ent. aerogenes | 1.56 | 1.56 | 1.56 | 1.56 | 1.56 |
| Ent. aerogenes NY-2 | >100 | >100 | >100 | >100 | >100 |
| Kleb. pneumoniae Y-11 | 3.13 | 3.13 | 12.5 | 25 | 6.25 |
| Kleb. pneumonia V-17 | 3.13 | 3.13 | 12.5 | 25 | 6.25 |
| Serratia marcesceus | 25 | 25 | >100 | 100 | 50 |
| Serratia marcesceus No. 10 | 50 | 25 | >100 | 100 | 50 |
| Prot. morganii Kono | 12.5 | 12.5 | >100 | 100 | 25 |
| Prot. rettgeri Y-1 | 50 | >100 | >100 | >100 | >100 |
| Citrobacter freundii | 50 | 6.25 | 100 | 100 | 50 |
| Pseud pyocyanea NCTC 10490 | >100 | >100 | 100 | >100 | >100 |

| | 16 | 17 | 18 | 19 | 20 |
|---|---|---|---|---|---|
| Staph. aureus 209P | 3.13 | 3.13 | 3.13 | 1.56 | 0.39 |
| E. coli NIHJ | 0.78 | 3.13 | 1.56 | <0.2 | <0.2 |
| E. coli Ebara | 3.13 | 6.25 | 3.13 | 0.78 | 3.13 |
| E. coli Takeda | 25 | 25 | 6.25 | 6.25 | 12.5 |
| Ent. cloacae | 3.13 | 6.25 | 3.13 | 1.56 | 0.78 |
| Ent. cloacae V-8 | >100 | >100 | >100 | 100 | >100 |
| Ent. aerogenes | 3.13 | 6.25 | 3.13 | 3.13 | 0.78 |
| Ent. aerogenes NY-2 | >100 | >100 | >100 | >100 | >100 |
| Kleb. pneumoniae Y-11 | 3.13 | 3.13 | 3.13 | 6.25 | 3.13 |
| Kleb. pneumoniae V-17 | 12.5 | 6.25 | 3.13 | 3.13 | 6.25 |
| Serratia marcesceus | >100 | >100 | 25 | 100 | 25 |
| Serratia marcesceus No. 10 | 50 | >100 | 50 | 25 | 25 |
| Prot. morganii Kono | 50 | 100 | 25 | 25 | 25 |
| Prot. rettgeri Y-1 | >100 | 100 | >100 | >100 | >100 |
| Citrobacter freundii | 50 | >100 | 50 | 50 | 100 |
| Pseud pyocyanea NCTC 10490 | >100 | >100 | >100 | >100 | >100 |

Table 2-continued

| | Ex. No. | | | | |
|---|---|---|---|---|---|
| | 21 | 22 | 23 | 25 | CEZ |
| Staph. aureus 209P | 0.39 | 0.78 | 0.39 | 3.13 | ≦0.2 |
| E. coli NIHJ | 0.39 | 1.56 | ≦0.2 | 1.56 | 1.56 |
| E. coli Ebara | 1.56 | 6.25 | 0.39 | 6.25 | 50 |
| E. coli Takeda | 6.25 | 12.5 | 0.78 | 100 | 12.5 |
| Ent. cloacae | 100 | 0.78 | ≦0.2 | 3.13 | ≦0.2 |
| Ent. cloacae V-8 | >100 | >100 | 100 | >100 | >100 |
| Ent. aerogenes | 0.78 | 0.78 | ≦0.2 | 3.13 | ≦0.2 |
| Ent. aerogenes NY-2 | >100 | >100 | 25 | >100 | 100 |
| Kleb. pneumoniae Y-11 | 3.13 | 6.25 | 0.78 | 50 | 3.13 |
| Kleb. neumonaie V-17 | 3.13 | 6.25 | 0.39 | 25 | >100 |
| Serratia marcesceus | 100 | 100 | 6.25 | >100 | >100 |
| Serratia marcesceus | 100 | >100 | 3.13 | 100 | >100 |
| Prot. morganii Kono | 100 | 100 | 12.5 | >100 | >100 |
| Prot. rettgeri Y-1 | >100 | >100 | >100 | >100 | >100 |
| Citrobacter freundii | 100 | >100 | 12.5 | 50 | 12.5 |
| Pseud pyrocyanaea NCTC 10490 | >100 | >100 | 100 | >100 | >100 |

(CEZ: Cefazolin)

The compounds of this invention are formed into formulation in a manner similar to other known cephalosporin derivatives and are administered orally or parenterally as, for example, in the form of tablets, powder, granules, troches injections, suppositories, suspensions, etc., and the dose thereof differs according to the severity of patients' diseases and the general conditions, ages, weights, etc., of patients but is usually 10–50 mg/Kg.

The invention will further be illustrated by the following examples.

EXAMPLE 1

A mixture of 100 mg. of 7β-bromoacetamido-7α-methoxy-3-(1-methyltetrazol-5-yl)thiomethyl-Δ³-cephem-4-carboxylic acid, 30 mg. of 2-hydroxy-4-mercaptopyridine, 40 mg. of sodium hydrogencarbonate, 5 ml. of water, and 10 ml. of methanol was stirred for 4.5 hours at room temperature. After distilling off methanol from the reaction mixture, the pH was adjusted to 9 with sodium hydrogen-carbonate and the mixture was filtered. The filtrate was acidified with 1.5% hydrochloric acid and extracted with 100 ml. of a mixture of n-butanol and ethyl acetate in a 1:1 ratio by volume. The extract was washed with a saturated aqueous solution of sodium chloride and water, and then a saturated aqueous solution of sodium chloride and dried over anhydrous magnesium sulfate. The solvent was distilled off under reduced pressure. The residue obtained was subjected to a gradient elution column chromatography using the initial solution of a mixture of chloroform, isopropanol, and formic acid in a 90:10:3 ratio by volume and subsequent increase of the % methanol as elution proceeds.

Then, the fractions containing the aimed compound were collected and the solvent was distilled off from the combined fractions to provide 57 mg. of 7β-[4-(2-hydroxypyridyl)] thioacetamido-7α-methoxy-3-(1-methyltetrazol-5-yl)thiomethyl-Δ³-cephem-4-carboxylic acid.

Nuclear magnetic resonance spcetra (D₆-DMSO) δ(p.p.m.): 3.38 (s, 3H), 3.66 (q, 2H), 3.84 (s, 3H), 3.92 (s, 3H), 4.30 (q, 2H), 5.06 (s, 1H), 6.06 (d, 1H), 6.20 (d, 1H), 6.20 (s, 1H), 7.22 (d, 1H).

EXAMPLE 2

(a) To 6 ml. of methylene chloride were added 39 mg. of triethylamine and 164 mg. of 7β-bromoacetamido-7α-methoxycephalosporanic acid, the mixture was stirred at room temperature and, after adding thereto 2.8 mg. of 4-mercaptopyridine under stirring, the resultant mixture was further stirred for 2 hours. After the reaction was over, the reaction mixture was cooled with ice for 30 minutes and the precipitates formed were recovered by filtration, washed with methylene chloride, and dried to provide 97 mg. of 7α-methoxy-7β-(4-pyridyl)thioacetamidocephalosporanic acid.

Nuclear magnetic resonance spectra (D₆-DMSO)

δ(p.p.m.): 2.02 (3H, —COCH₃),
3,40 (3H, —OCH₃), 3,97 (2H, —SCH₂CO—),

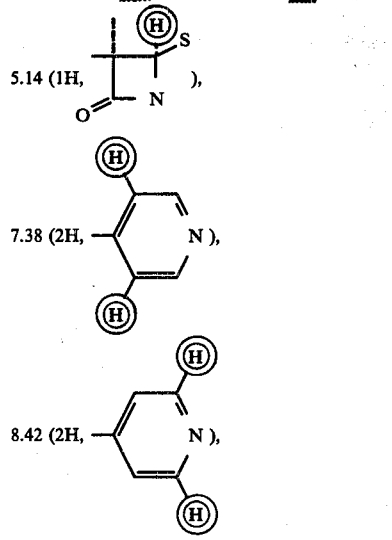

5.14 (1H, ), 7.38 (2H, ), 8.42 (2H, ), (b) In a mixture of 5 ml. of methylene chloride and 19.5 mg. of triethylamine was dissolved 92 mg. of 7-bromoacetamido-7β-methoxy-3-(1-methyltetrazol-5-yl)thiomethyl-Δ³-cephem-4-carboxylic acid with stirring at room temperature and after further adding thereto 22 mg. of 4-mercaptopyridine, the resultant mixture was stirred for about 40 minutes. The precipitates formed were recovered by filtration, washed with ethylene chloride and dried to provide 58 mg. of 7α-methoxy-3-(1-methyltetrazol-5-yl)thiomethyl-7β-(4-pyridyl)thioacetamido-Δ³-cephem-4-carboxylic acid.

Nuclear magnetic resonance spectra (D₆-DMSO)

δ(p.p.m.): 3,33 (3H, —OCH₃), 3,93 (5H, —SCH₂CO—, and

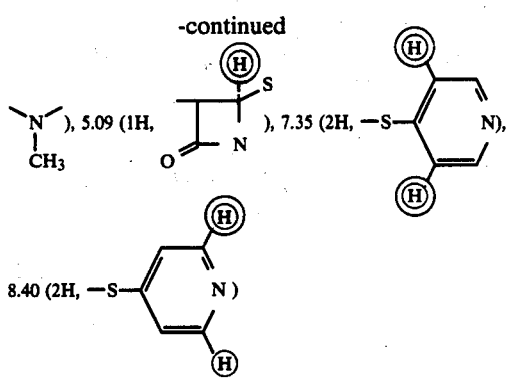

EXAMPLE 3

In a mixture of 5 ml. of methylene chloride and 22.0 mg. of triethylamine was dissolved 100 mg. of 7β-bromoacetamido-7β-methoxy-3-(5-methyl-1,3,4-thiadiazol-2-yl)-thiomethyl-Δ³-cephem-4-carboxylic acid with stirring at room temperature and then the solution was treated as in Example 2-b) to provide 60 mg. of 7β-methoxy-3-(5-methyl-1,3,4-thiadiazol-2-yl)thiomethyl-7β-(4-pyridyl)thioacetamido-Δ³-cephem-4-carboxylic acid.

Nuclear magnetic resonance spectra (D₆-DMSO)

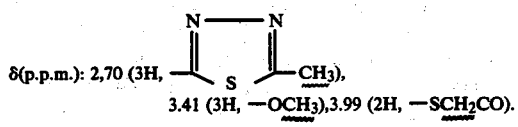

3.41 (3H, —OCH₃), 3.99 (2H, —SCH₂CO).

EXAMPLE 4

A mixture of 200 mg. of 7β-bromoacetamido-7α-methoxy-3-(5-methyl-1,3,4-thiadiazol-2-yl)thiomethyl-Δ³-cephem-4-carboxylic acid, 65 mg. of 2-hydroxy-4-mercaptopyridine, 8 ml. of water, and 16 ml. of methanol was stirred on an ice bath and, after further adding to the mixture 80 mg. of sodium hydrogencarbonate, the resultant mixture was stirred for 2 hours at room temperature. Then, methanol was distilled off under reduced pressure, and after filtering, the filtrate was acidified with diluted hydrochloric acid and extracted with 50 ml. of a mixture of n-butanol and ethyl acetate of 1:1 by volume ratio. The extract was washed with a saturated aqueous solution of sodium chloride, dried over anhydrous magnesium sulfate, and the solvent was distilled off from the residue to provide 210 mg. of 7β-(2-hydroxy-4-pyridyl)thioacetamido-7β-methoxy-3-(5-methyl-1,3,4-thiadiazol-2-yl)thiomethyl-Δ³-cephem-4-carboxylic acid.

Nuclear magentic resonance spectra (D₆-DMSO) δ(p.p.m.): 2.70 (s, 3H), 3.42 (s, 3H), 3.72 (q, 2H), 3.84 (s, 2H), 4.36 (q, 2H), 5.12 (s, 1H), 6.10 (d, 1H), 6.24 (s, 1H), 7.26 (d, 1H).

EXAMPLE 5

To a mixture of 120 mg. of 3-hydroxy-4-mercaptopyridine, 140 mg. of sodium hydrogencarbonate, 15 ml. of methanol, and 7.5 ml. of water was added 360 mg. of 7β-bromoacetamido-7α-methoxy-3-(1-methyltetrazol-5-yl)thiomethyl-Δ³-cephem-4-carboxylic acid and the mixture was stirred under ice-cooling and after raising the temperature to room temperature, was further stirred for 2 hours.

After distilling off methanol, the reaction mixture was filtered and the filtrate was acidified with 2 ml. of 1 N hydrochloric acid. The precipitates thus formed were recovered by filtration, washed with water and dried to provide 200 mg. of 7β-(3-hydroxy-4-pyridyl)-thioacetamido-7α-methoxy-3-(1-methyltetrazol-5-yl)thiomethyl-Δ³-cephem-4-carboxylic acid as a crude product.

Meanwhile, the aqueous layer formed in the aforesaid procedure was extracted with 50 ml. of a mixture of n-butanol and methanol in a 1:1 ratio by volume and the organic layer was recovered, washed twice with saturated aqueous sodium chloride, dried over anhydrous magnesium sulfate, and then the solvent was distilled off to provide 280 mg. of the crude product shown above.

By applying silica gel column chromatography to the crude product obtained from the aqueous layer using a mixture of chloroform, isopropanol, formic acid, and methanol in a 30:3:1:8 ratio by volume as the developing solvent, 100 mg. of the pure product was obtained.

Nuclear magnetic resonance spectra (D₆-DMSO)

δ(p.p.m.): 3.40 (s, 3H, 7-OCH₃), 3.94 (s, 3H, N—CH₃), 4.06 (s, 2H, —S—CH₂CO), 4.30 (q, 2H), 5.10 (s, 1H, 6-H),

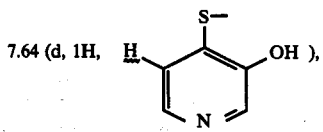

EXAMPLE 6

To a solution of 100 mg. of 7β-bromoacetamido-7α-methoxy-3-(1-methyltetrazol-5-yl)thiomethyl-Δ³-cephem-4-carboxylic acid in 3 ml. of methanol was added a solution of 62.5 mg. of 2-amino-5-mercapto-1,3,4-thiadiazole and 0.066 ml. of triethylamine in 3 ml. of methanol and the solution was stirred for 30 minutes at room temperature. The solvent was distilled off from the reaction mixture under reduced pressure and the residue formed was subjected to silica gel column chromatography using a mixture of methylene chloride, methanol, formic acid in a 80:20:2 ratio by volume as the developing solvent. The fractions containing the aimed compound were combined and the solvent was distilled off to provide 60 mg. of 7β-(5-imino-4,5-dihydro-1,3,4-thiadiazol-2-yl)thioacetamido-7α-methoxy-3-(1-methyltetrazol-5-yl)thiomethyl-Δ³-cephem-4-carboxylic acid.

Nuclear magnetic resonance spectra (D₆-DMSO)

δ(p.p.m.):

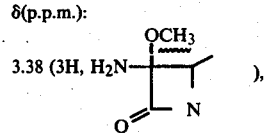

-continued 3.92 (3H, 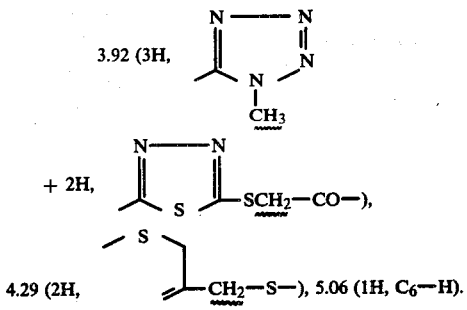

+ 2H, 4.29 (2H, —CH₂—S—), 5.06 (1H, C₆—H).

EXAMPLE 7

To a solution of 100 mg. of 7β-bromoacetamido-7α-methoxy-3-(1-methyltetrazol-5-yl)thiomethyl-Δ³-cephem-4-carboxylic acid in 5 ml. of methanol was added a soluion of sodium salt of 5-mercapto-2-oxo-2,3-dihydro-1,3,4-thiadiazole in 3 ml. of methanol prepared by dissolving 60 mg. of 5-mercapto-2-oxo-2,3-dihydro-1,3,4-thiadiazole and 0.59 ml. of a 1 N aqueous sodium hydroxide solution in 2 ml. of methanol, and distilling off the solvent therefrom. After stirring the mixture for 30 minutes at room temperature, the solvent was distilled off under reduced pressure and the residue obtained was subjected to a column chromatography using a mixture methanol and ethyl acetate in a 1:4 ratio by volume as a developing solvent for removing impurities and then a mixture of methanol and ethyl acetate in a 1:2 ratio by volume as a developing solvent for the product.

The fractions containing the aimed compound were combined and then the solvent was distilled off from the combined solution to provide 70 mg. of 7β-(5-oxo-4,5-dihydro-1,3,4-thiadiazol-2-yl)thioacetamido-7α-methoxy-3-(1-methyltetrazol-5-yl)thiomethyl-Δ³-cephem-4-carboxylic acid.

Nuclear magnetic resonance spectra (D₆-DMSO)

δ(p.p.m.): 3,40 (3H, C₇—OCH₃), 3.94 (3H, 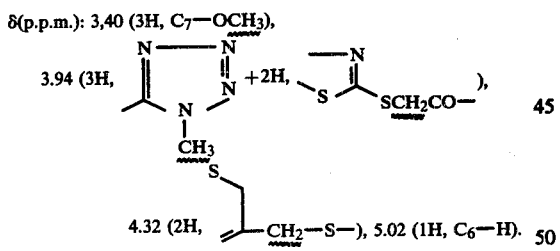

4.32 (2H, —CH₂—S—), 5.02 (1H, C₆—H).

EXAMPLE 8

(a) A solution of 226 mg. of 4-thioxo-2-thiazolidinone in 5 ml. of methanol was cooled to −10° C. and after adding thereto 344 mg. of triethylamine, the resultant solution was added to a solution of 718 mg of 7β-bromoacetamido-7α-methoxycephalosporanic acid in 5 ml. of methanol at temperatures below −5° C. After carrying out the reaction for 2 hours at temperatures of between −5° C. and 0° C., the solvent was distilled off at low temperature under reduced pressure and the residue formed was subjected to a silica gel column chromatography using a mixture of chloroform, isopropanol, and formic acid in a 90:10:2 ratio by volume as a developing solvent.

The fractions containing the aimed compound were combined and the solvent was distilled off to provide 860 mg. of 7α-methoxy-7β-(2-oxo-Δ⁴-thiazolin-4-yl)thioacetamidocephalosporanic acid.

Nuclear magnetic resonance spectra (D₆-acetone)

δ(p.p.m.): 2.04 (3H), 3.52 (3H, C₇—OCH₃), 3,31–3.62 (2H, 2-position), 3.81 (2H, —S—CH₂—CO—), 4,97 (2H, C₃—CH₂OCOCH₃), 5.15 (1H, 6-position), 6.51 (1H, 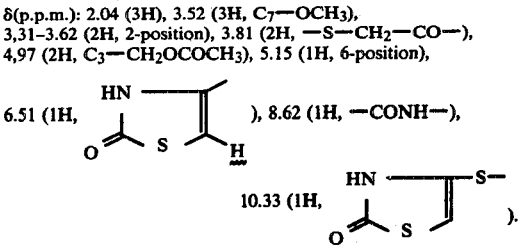 ), 8.62 (1H, —CONH—), 10.33 (1H, ).

(b) To 27 ml. of a phosphate buffer solution having a pH of 6.86 were added 484 mg. of 7α-methoxy-7β-(2-oxo-Δ⁴-thiazolin-4-yl)thioacetamidocephalosporanic acid, 118.4 mg. of 5-mercapto-1-methyltetrazole, and 85.7 mg. of sodium hydrogencarbonate and then the reaction was carried out for 18 hours at 58°–60° C. After the reaction was over, the pH of the reaction mixture was adjusted to pH 1–2 by adding thereto a 40% aqueous phosphoric acid solution under ice-cooling and the the product was extracted twice each with 30 ml. of ethyl acetate. The extracts were combined, washed with water, dried over anhydrous sodium sulfate, and then the solvent was distilled off under reduced pressure. The residue formed was subjected to a silica gel column chromatography using a mixture of chloroform, isopropanol, and formic acid in a 80:20:2 ratio by volume as a developing solvent.

The fractions containing the aimed compound were combined and the solvent was distilled off to provide 60 mg. of 7α-methoxy-3-(1-methyltetrazol-5-yl)thiomethyl-7β-(2-oxo-Δ⁴-thiazolin-4-yl)thioacetamido-Δ³-cephem-4-carboxylic acid.

Nuclear magnetic resonance spectra (D₆-acetone)

δ(p.p.m.): 3.52 (3H, C₇—OCH₃), 3.60–4.00 (4H,

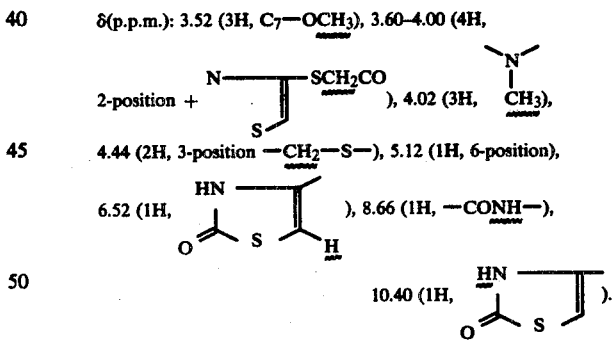

4.44 (2H, 3-position —CH₂—S—), 5.12 (1H, 6-position), 6.52 (1H, ), 8.66 (1H, —CONH—), 10.40 (1H, ).

EXAMPLE 9

To 4 ml. of methylene chloride was added 21.1 mg. of triethylamine and then 100 mg. of 7β-bromoacetamido-7α-methoxy-3-(1-methyltetrazol-5-yl)thiomethyl-Δ³-cephem-4-carboxylic acid was dissolved with stirring at room temperature. To the solution was further added 34 mg. of 2,5-dimercapto-1,3,4-thiadiazole and after adding dropwise a few drops of methanol for dissolving the 2,5-dimercapto-1,3,4-thiadiazole, the resultant mixture was stirred for about 3 hours. After the reaction was over, the solvent was distilled off from the reaction mixture, and to the residue formed were added 40 ml. of ethyl acetate and diluted hydrochloric acid to acidify it, whereby an ethyl acetate layer and an aqueous layer formed. The ethyl acetate layer formed was recovered, washed with water, dried over anhydrous sodium sulfate, and then the solvent was distilled off under reduced pressure. The residue obtained was subjected to a silica gel column chromatography using a mixture of chloroform, methanol, and formic acid of 50:4:1 ratio by volume as a developing solvent. The fractions containing the aimed compound were combined and the solvent was distilled off to provide 60 mg. of 7β-(4,5-dihydro-5-thioxo-1,3,4-thiadiazol-2-yl)-thioacetamido-7α-methoxy-3-(1-methyltetrazol-5-yl)thiomethyl-Δ³-cephem-4-carboxylic acid.

Nuclear magnetic resonance spectra (D₆-acetone)

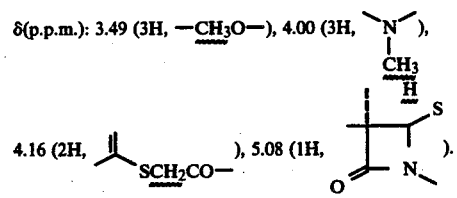

EXAMPLE 10

In a mixture of 0.627 ml. of a 1 N (f=0.998) aqueous sodium hydroxide solution and 1.5 ml. of methanol was dissolved 110 mg. of 5-acetamido-2-mercapto-1,3,4-thiadiazole followed by stirring for several minutes and then the solvent was distilled off. The white solid residue obtained was dissolved in 2.5 ml. of methanol and after adding to the solution a solution prepared by dissolving 200 mg. of 7β-bromoacetamido-7α-methoxy-3-(1-methyltetrazol-5-yl)thiomethyl-Δ³-cephem-4-carboxylic acid in 2.5 ml. of methanol at room temperature, the resultant mixture was stirred for 30 minutes at room temperature. Then, the solvent was distilled off and the residue obtained was subjected to a silica gel column chromatography using a mixture of chloroform isopropyl alcohol, and formic acid in a 90:10:3 ratio by volume to elute unchanged 5-acetamido-2-mercapto-1,3,4-thiadiazole. Thereafter, the product was eluted using as an eluent, a mixture of chloroform, methanol, and formic acid in a 90:10:2 ratio by volume.

The fractions containing the aimed compound were combined and the solvent was distilled off to provide 150 mg. of the light-yellow powder of 7β-(5-acetylimino-4,5-dihydro-1,3,4-thiadiazol-2-yl)thioacetamido-7α-methoxy-3-(1-methyltetrazol-5-yl)thiomethyl-Δ³-cephem-4-carboxylic acid.

Nuclear magnetic resonance spectra (D₆-DMSO)

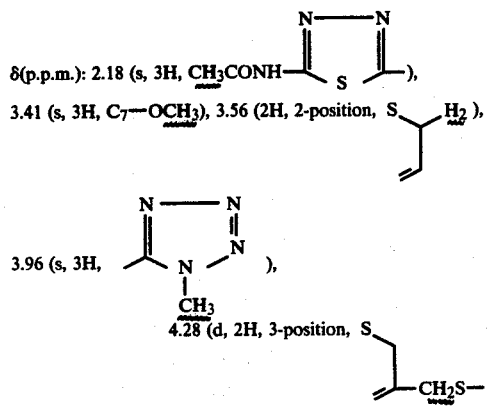

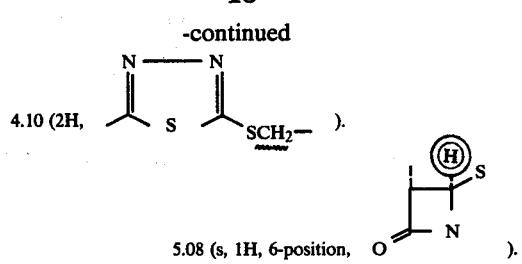

EXAMPLE 11

To a solution of 192 mg. of 7β-bromoacetamido-7α-methoxy-3-(1-methyltetrazol-5-yl)thiomethyl-Δ³-cephem-4-carboxylic acid in 5 ml. of methanol was added a solution prepared by dissolving 89.5 mg. of 1,3-thiazoline-2,4-dithione and 113 μl. of triethylamine in 2 ml. of methanol at −5° C. After performing the reaction for 2 hours at temperatures between −5° C. and 5° C., the solvent was distilled off under reduced pressure and the residue obtained was subjected to a silica gel column chromatography using a mixture in a chloroform, methanol, and formic acid of 85:15:2 ratio by volume as the eluent.

The fractions containing the aimed compound were combined and the solvent was distilled off. The residue thus obtained was homogenized by acetone and then solidified by the addition of ether to give a powdery material, which was recovered by filtration and dried to provide 84.2 mg. of 7α-methoxy-3-(1-methyltetrazol-5-yl)thiomethyl-7β-(2-thioxo-Δ³-thiazolin-4-yl)thioacetamido-Δ³-cephem-4-carboxylic acid.

Nuclear magnetic resonance spectra (D₆-DMSO)

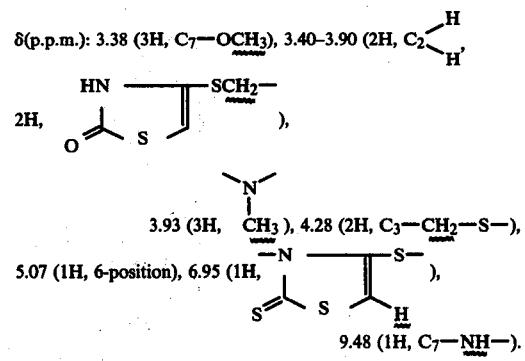

EXAMPLE 12

In 5 ml. of methanol was dissolved 200 mg. of 7β-bromoacetamido-7α-methoxy-3-(1-methyltetrazol-5-yl)thiomethyl-Δ³-cephem-4-carboxylic acid and then to the solution was added a solution of 110 mg. of 1-methylamino-5-mercapto-1,3,4-thiadiazole sodium salt in 3 ml. of methanol.

The mixture was stirred for 30 minutes at room temperature, the solvent was distilled off under reduced pressure, and the residue obtained was subjected to a silica gel column chromatography to initially remove excessive 1-methylamino-5-mercapto-1,3,4-thiadiazole using a mixture of chloroform, isopropanol and formic acid in a 90:10:2 ratio by volume. The product was then eluted using a mixture of chloroform, methanol, and formic acid in a 80:20:10 ratio by volume as a developing solvent. The fractions containing the aimed material were combined and after distilling off the solvent under reduced pressure, the residue obtained was dried to provide 100 mg. of 7α-methoxy-7β-(5-methylamino-1,3,4-thiadiazol-2-yl)thioacetamido-3-(1-methyltetrazol-5-yl)thiomethyl-Δ³-cephem-4-carboxylic acid.

Nuclear magnetic resonance spectra (D₆-DMSO)

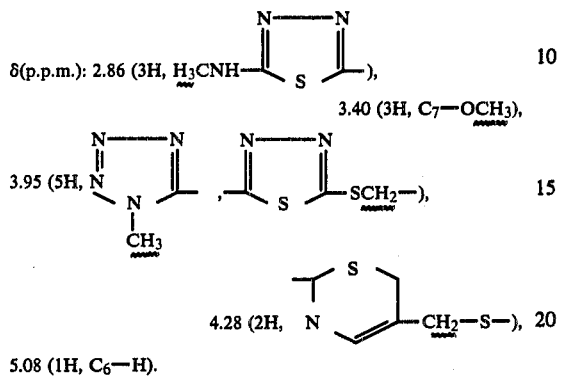

EXAMPLE 13

In 5 ml. of methanol was dissolved 200 mg. of 7β-bromoacetamido-7α-methoxy-3-(5-methyl-1,3,4-thiadiazol-2-yl)thiomethyl-Δ³-cephem-4-carboxylic acid and to the solution was added a solution of 100 mg. of 1-methylamino-5-mercapto-1,3,4-thiadiazole sodium salt in 3 ml. of methanol.

Thereafter, the mixture was treated as in Example 12 to provide 80 mg. of 7β-(5-methylamino-1,3,4-thiadiazol-2-yl)-thioacetamido-7α-methoxy-3-(5-methyl-1,3,4-thiadiazol-2-yl)thiomethyl-Δ³-cephem-4-carboxylic acid.

Nuclear magnetic resonance spectra (D₆-DMSO)

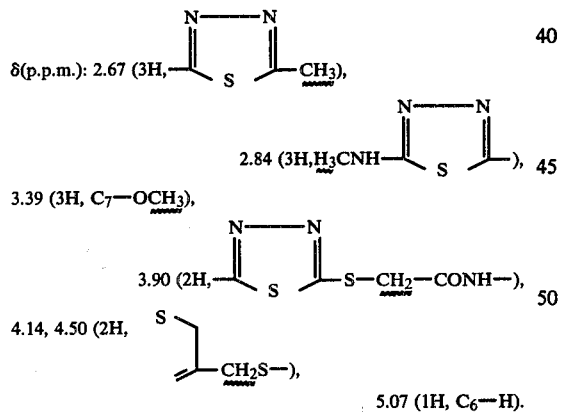

EXAMPLE 14

In 5 ml. of methanol was dissolved 200 mg. of 7β-bromoacetamido-7α-methoxy-3-(1-methyltetrazol-5-yl)-thiomethyl-Δ³-cephem-4-carboxylic acid and to the solution was added a solution of 150 mg. of 1-ethoxycarboxamido-5-mercapto-1,3,4-thiadiazole sodium salt in 3 ml. of methanol. Then, the mixture was treated as in Example 12 to provide 110 mg. of 7β-(5-ethoxycarboxamido-1,3,4-thiadiazol-2-yl)-thioacetamido-7α-methoxy-2-(1-methyltetrazol-5-yl)thiomethyl-Δ³-cephem-4-carboxylic acid.

Nuclear magnetic resonance spectra (D₆-DMSO)

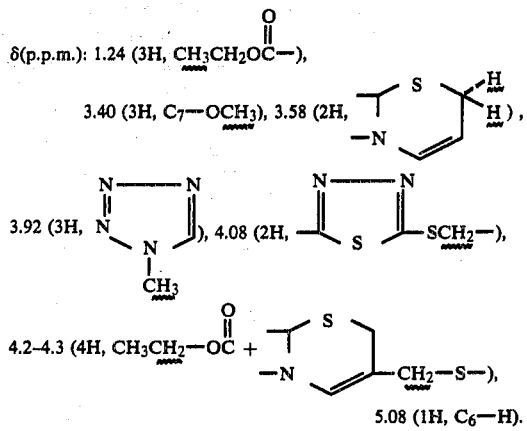

EXAMPLE 15

In 5 ml. of methanol was dissolved 200 mg. of 7β-bromoacetamido-7α-methoxy-3-(1-methyltetrazol-5-yl)thiomethyl-Δ³-cephem-4-carboxylic acid and to the solution was added a solution of 140 mg. of 1-methoxycarboxamido-5-mercapto-1,3,4-thiadiazole sodium salt in 3 ml. of methanol.

The mixture was, then, treated as in Example 12 to provide 150 mg. of 7α-methoxy-7β-(5-methoxycarboxamido-1,3,4-thiadiazol-2-yl)thioacetamido-3-(1-methyltetrazol-5-yl)thiomethyl-Δ³-cephem-4-carboxylic acid.

Nuclear magnetic resonance spectra (D₆-DMSO)

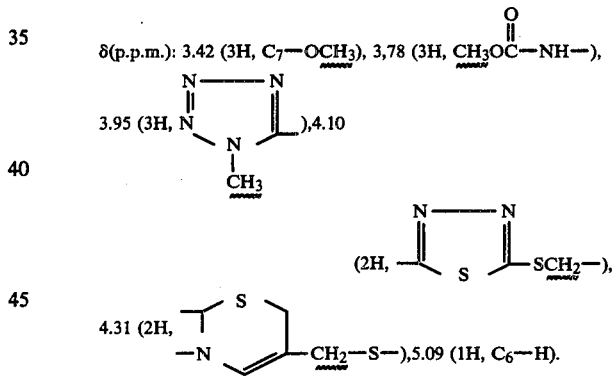

EXAMPLE 16

To a solution of 100 mg. of 7β-bromoacetamido-7α-methoxy-3-(1-methyltetrazol-5-yl)thiomethyl-Δ³-cephem-4-carboxylic acid in 5 ml. of methanol was added a solution of 27.5 mg. of 5-amino-2-mercaptothiazole and 0.058 ml. of triethylamine in 2 ml. of methanol under nitrogen gas stream. After stirring the mixture for 30 minutes at room temperature, the solvent was distilled off under reduced pressure and the residue obtained was subjected to a silica gel column chromatography and then the product was developed using a mixture of chloroform, methanol, and formic acid in a 85:15:2 ratio by volume. Then, the fractions containing the aimed compound were collected and the solvent was distilled off to provide 37 mg. of 7β-[(5-aminothiazol-2-yl)thioacetamido]-7α-methoxy-3-(1-methyltetrazol-5-yl)thiomethyl-Δ³-cephem-carboxylic acid.

Nuclear magnetic resonance spectra (D₆-DMSO)

δ(p.p.m.):

3.40 (3H, 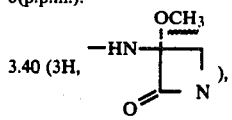), 3.96 (3H, 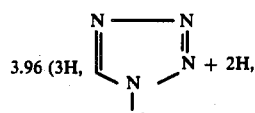 + 2H,

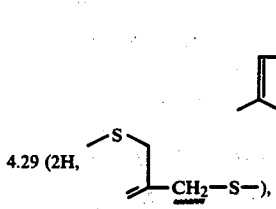

4.29 (2H, 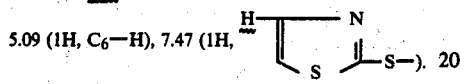

5.09 (1H, C₆—H), 7.47 (1H, 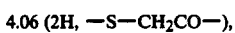

EXAMPLE 17

In 15 ml. of methylene chloride were dissolved 50 mg. of triethylamine, 70 mg. of 2,5-dimercapto-1,3,4-thiadiazole, and 1 ml. of methanol and to the solution was added 200 mg. of 7β-bromoacetamido-7α-methoxy-3-(5-methyl-1,3,4-thiadiazol-2-yl)thiomethyl-Δ³-cephem-4-carboxylic acid followed by stirring for about 1 hour at room temperature. After the reaction was over, the solvent was distilled off under reduced pressure and after adding to the residue obtained a diluted aqueous hydrochloric acid solution, the product was extracted with 50 ml. of a mixture of n-butanol and ethyl acetate in a 1:1 ratio by volume. The extract was washed with saturated aqueous sodium chloride solution, dried over anhydrous magnesium chloride, and then the solvent was distilled off under reduced pressure. The residue obtained was subjected to a silica gel column chromatography and developed using a mixture of chloroform, methanol, and formic acid in a 100:5:1 ratio by volume. Then, the fractions containing the aimed compound were collected and the solvent was distilled off to provide 120 mg. of 7β-(4,5-dihydro-5-thioxo-1,3,4-thiadiazol-2-yl)thioacetamido-7α-methoxy-3-(5-methyl-1,3,4-thiadiazol-2-yl)thiomethyl-Δ³-cephem-4-carboxylic acid.

Nuclear magnetic resonance spectra (D₆-DMSO)

δ(p.p.m.):

2.69 (3H, 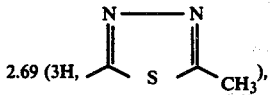

4.06 (2H, —S—CH₂CO—), 3.42 (3H, —OCH₃), 5.12 (1H, ).

EXAMPLE 18

In 3 ml. of water were dissolved 140 mg. of 2-mercapto-1,3,4-thiadiazol-5-yl-thioacetic acid and 72 mg. of sodium carbonate and to the solution was added a solution of 250 mg. of 7β-bromoacetamido-7α-methoxy-3-(1-methyltetrazol-5-yl)thiomethyl-Δ³-cephem-4-carboxylic acid in about 6 ml. of methanol with stirring under ice-cooling followed by further stirring for 2 hours.

After the reaction was over, the reaction mixture was concentrated under reduced pressure to distill off methanol and after acidifying the concentrate by the addition of diluted aqueous hydrochloric acid solution, the product was extracted twice each with 30 ml. of a mixture of n-butanol and ethyl acetate of 1:1 by volume ratio. The extracts were combined, washed with saturated sodium chloride solution, dried over anhydrous magnesium sulfate, and then the solvent was distilled off under reduced pressure. The residue formed was subjected to silica gel column chromatography and developed with a mixture of chloroform, methanol, and formic acid in a 100:8:1 ratio by volume. The fractions containing the aimed material were collected, the solvent was distilled off under reduced pressure, and the residue was dried to provide about 140 mg. of 7β-(5-carboxymethylthio-1,3,4-thiadiazol-2-yl)thioacetamido-7α-methoxy-3-(1-methyltetrazol-5-yl)thiomethyl-Δ³-cephem-4-carboxylic acid.

Nuclear magnetic resonance spectra (D₆-DMSO)

δ(p.p.m.): 3.40 (3H, —OCH₃), 3.93 (3H, >N—CH₃), 4.12 (4H, HO₂CCH₂—S—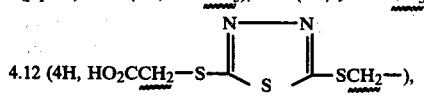

5.08 (1H, 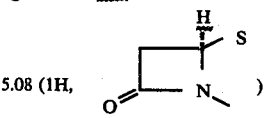)

EXAMPLE 19

In 5 ml. of methanol was dissolved 200 mg. of 7β-bromoacetamido-7α-methoxy-3-(1-methyltetrazol-5-yl)thiomethyl-Δ³-cephem-4-carboxylic acid and to the solution was added a solution of 130 mg. of 2-mercapto-5-(3-methylureido)-1,3,4-thiadiazole sodium salt in 3 ml. of methanol.

The mixture was stirred for 30 minutes at room temperature, the solvent was distilled off from the reaction mixture under reduced pressure, and the residue obtained was subjected to silica gel column chromatography to initially remove excessive 2-mercapto-5-(3-methylureido)-1,3,4-thiadiazole using a mixture of chloroform, isopropanol, and formic acid in a 90:10:2 ratio by volume and then develop the product using a mixture of chloroform, methanol, and formic acid in a 80:20:1 ratio by volume. The fractions containing the aimed product were collected, the solvent was distilled off under reduced pressure, and then the residue was solidified by the addition of 20 ml. of ether to provide 140 mg. of 7α-methoxy-3-(1-methyltetrazol-5-yl)-thiomethyl-7β-[5-(3-methylureido)-1,3,4-thiadiazol-2-yl]-thioacetamido-Δ³-cephem-4-carboxylic acid.

Nuclear magnetic resonance spectra (D₆-DMSO)

δ(p.p.m.):

2.72 (3H, CH₃—NH—C(=O)—NH—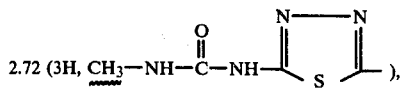), 3.44 (3H, C₇—OCH₃), about 3.60 (2H, C₂—H), 3.97 (3H, 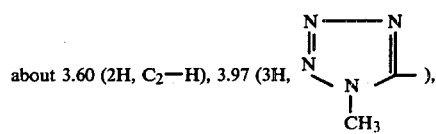), 4.07 (2H, 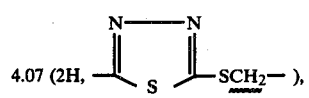SCH₂— ), 4.30 (2H, —N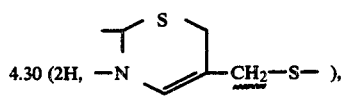CH₂—S— ), 5.10 (1H, C₆—H).

EXAMPLE 20

In about 4 ml. of water were dissolved 115 mg. of 2-hydroxy-4-mercapto-5-methylpyridine and 76 mg. of sodium hydrogencarbonate and to the solution was added a solution of 300 mg. of 7β-bromoacetamido-7α-methoxy-3-(1-methyltetrazol-5-yl)thiomethyl-Δ³-cephem-4-carboxylic acid in 10 ml. of methanol with stirring under ice-cooling followed by further stirring for about 40 minutes.

After the reaction was over, the reaction mixture was concentrated under reduced pressure to distill off methanol almost completely and about 20 ml. of water was added to the concentrate. After acidifying the solution with 1 N hydrochloric acid under ice-cooling, the product was extracted twice each with about 50 ml. of a mixture of n-butanol and ethyl acetate in a 1:1 ratio by volume. The combined extracts were washed with aqueous saturated sodium chloride solution and dried over anhydrous magnesium sulfate, and then the solvent was distilled off under reduced pressure. The residue formed was subjected to a silica gel column chromatography and developed with a mixture of chloroform, methanol, and formic acid in a 100:8:1 ratio by volume. The fractions containing the aimed material were combined and 24 mg. of 7β-(2-hydroxy-5-methyl-4-pyridyl)thioacetamido-7α-methoxy-3-(1-methyl-tetrazol-5-yl)thiomethyl-Δ³-cephem-4-carboxylic acid was obtained.

Nuclear magnetic resonance spectra (D₆-DMSO)

δ(p.p.m.): 1.96 (3H 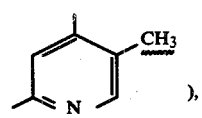), 3.39 (3H, CH₃O— ), about 3.90 (2H, —SCH₂CO— ), 3.93 (3H, CH₃—N⟨ ), 5.09 (1H, 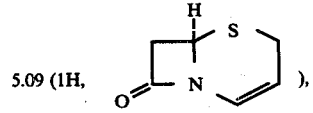), 6.20 (1H, 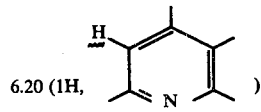)

and 7.11 (1H, 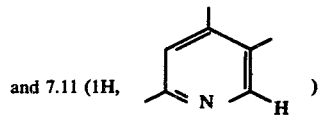)

EXAMPLE 21

In 2 ml. of water was suspended 120 mg. of 2-hydroxy-4-mercapto-3-methylpyridine and then 1.1 ml. of a 1 N aqueous sodium hydroxide solution was added to the suspension to dissolve completely the methylpyridine. Then, 300 mg. of 7β-bromoacetamido-7α-methoxy-3-(1-methyltetrazol-5-yl)thiomethyl-Δ³-cephem-4-carboxylic acid in 10 ml. of methanol was added to the solution prepared above with stirring under ice-cooling and the mixture was stirred for about 40 minutes under the same condition. After the reaction was over, the reaction mixture was concentrated under reduced pressure to distill off methanol almost completely and then about 20 ml. of water was added to the residue. The residue was then acidified with 1 N hydrochloric acid under ice-cooling and extracted twice each with about 50 ml. of a mixture of n-butanol and ethyl acetate in a 1:1 ratio by volume. The extracts were combined, washed with saturated aqueous sodium chloride solution, dried over anhydrous magnesium sulfate, and the solvent was distilled off under reduced pressure. The residue obtained was subjected to a silica gel column chromatography using a mixture of chloroform, methanol, and formic acid in a 100:10:1 ratio by volume as a developing solvent. The fractions containing the aimed material were combined to provide 200 mg. of 7β-(2-hydroxy-3-methyl-4-pyridyl)thioacetamido-7α-methoxy-3-(1-methyltetrazol-5-yl)thiomethyl-Δ³-cephem-4-carboxylic acid.

Nuclear magnetic resonance spectra (D₆-DMSO)

δ(p.p.m.):

1.96 (3H, 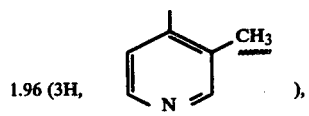), about 3.87 (2H, —S—CH₂CO— ), 3.38 (3H, CH₃—O— ), 3.93 (3H, CH₃—N⟨ ), 5.09 (1H, 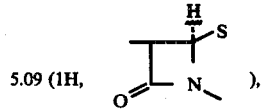), 6.25 (1H, 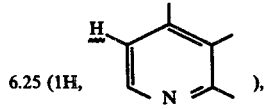), 7.11 (1H, 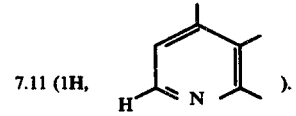).

EXAMPLE 22

In the manner of Example 20, 4-mercapto-3-methylpyridine N-oxide was used instead of 2-hydroxy-4-mercapto-5-methylpyridine, and as developing solvent of silica gel column chromatography a mixture of chloroform, methanol and formic acid in a 100:20:1 ratio by volume was used, and the other reaction conditions were same as Example 20. Whereby, 220 mg. of 7α-methoxy-7β-(3'-methyl-4'-pyridyl)thioacetamido-3-(1-methyltetrazol-5-yl)-thiomethyl-Δ³-cephem-4-carboxylic acid 1'-oxide was obtained.

Nuclear magnetic resonance spectra (D₆-DMSO)

δ(p.p.m.):

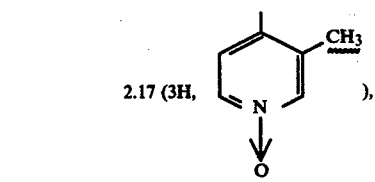
2.17 (3H, ), 3.37 (3H, CH₃O—) about 3.94 (5H, CH₃N<, —SCH₂CO—),

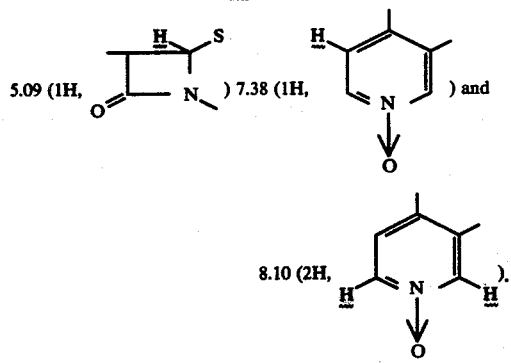
5.09 (1H, ) 7.38 (1H, ) and
8.10 (2H, ).

EXAMPLE 23

In about 1 ml. of water was dissolved 33 mg. of sodium carbonate and to the aqueous solution was added a solution of 300 mg. of 7β-bromoacetamido-7α-methoxy-3-(1-methyltetrazol-5-yl)-thiomethyl-Δ³-cephem-4-carboxylic acid in about 6 ml. of methanol with stirring under ice-cooling. Thereafter, a solution of 105 mg. of 2-amino-4-mercaptopyridine sodium salt in about 5 ml. of methanol was added dropwise over a period of about 20 minutes to the mixture prepared in the above step with stirring under ice-cooling and then the mixture was stirred for about 10 minutes to complete the reaction. Then, the reaction mixture was concentrated under reduced pressure, about 10 ml. of water was added to the residue to dissolve the product, and undissolved matters were filtered off. The filtrate was neutralized with 1 N hydrochloric acid under ice-cooling and the precipitates formed were recovered by filtration, washed with water and then methanol, and dried over phosphorus pentoxide under reduced pressure to provide about 200 mg. of 7β-(2-amino-4-pyridyl)thioacetamido-7α-methoxy-3-(1-methyltetrazol-5-yl)thiomethyl-Δ³-cephem-4-carboxylic acid.

Nuclear magnetic resonance spectra (D₂O+Na₂CO₃)

δ(p.p.m.):

3.46 (3H, CH₃—O—), about 3.96 (5H, CH₃N<,

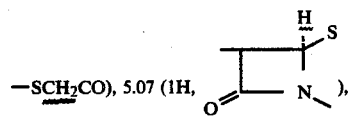
—SCH₂CO), 5.07 (1H, ),

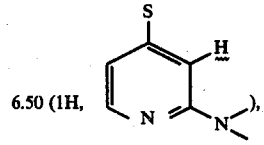
6.50 (1H, ),

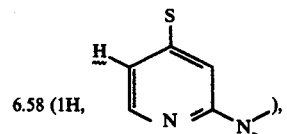
6.58 (1H, ),

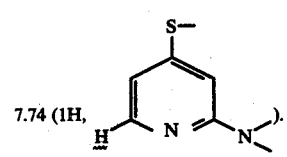
7.74 (1H, ).

EXAMPLE 24

To the mixture of 40 mg. of 2,6-dihydroxy-4-mercaptopyridine, 50 mg. of sodium hydrogencarbonate, 5 ml. of water and 10 ml. of methanol was added 140 mg. of 7β-bromoacetamido-7α-methoxy-3-(1-methyltetrazol-5-yl)thiomethyl-Δ³-cephem-4-carboxylic acid with stirring under ice-cooling. The resultant mixture was heated to room temperature and stirred for 2 hours. After distilling off methanol, the residue was acidified with 2 ml. of 1 N hydrochloric acid and the product was extracted with 30 ml. of a mixture of n-butanol and ethyl acetate in a 1:1 ratio by volume, washed three times with aqueous satureted sodium chloride solution, and dried over anhydrous magnesium sulfate. After distilling off the solvent, crude 7β-(2,6-dihydroxy-4-pyridyl)thioacetamido-7α-methoxy-3-(1-methyltetrazol-5-yl)-thiomethyl-Δ³-cephem-4-carboxylic acid was obtained. This crude product was subjected to a silica gel column chromatography using a mixture of chloroform, isopropyl alcohol and formic acid in a 90:10:3 ratio by volume as developing solvent, whereby 50 mg. of pure product was obtained.

Nuclear magnetic resonance spectra (D₆-DMSO)

δ(p.p.m.):

3.36 (3H, s, —OCH₃), 3.92 (3H, s, >N—CH₃),

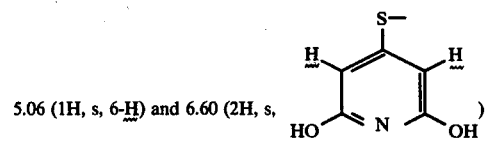
5.06 (1H, s, 6-H) and 6.60 (2H, s, )

EXAMPLE 25

In about 2 ml. of water was suspended 120 mg. of 3-hydroxy-2-mercapto-6-methylpyridine and then 1.2 ml. of a 1 N aqueous sodium hydroxide solution was added to the suspension to dissolve the methylpyridine. To the solution was added a solution of 300 mg. of 7β-bromoacetamido-7α-methoxy-3-(1-methyltetrazol-5-yl)thiomethyl-Δ³-cephem-4-carboxylic acid in about 10 ml. of methanol with stirring under ice-cooling followed by further stirring for about 40 minutes under ice-cooling to ensure the reaction. After distilling off methanol almost completely from the reaction mixture under reduced pressure, about 10 ml. of water was added to the residue and after acidifying the mixture by adding 1 N hydrochloric acid under ice-cooling, the product was extracted with about 150 ml. of ethyl acetate. The extract was dried over anhydrous magnesium sulfate and the solvent was distilled off under reduced pressure. Then, the residue formed was subjected to a silica gel column chromatography and developed using a mixture of chloroform, methanol, and formic acid in a 100:7:1 ratio by volume. The fractions containing the aimed material were combined to provide about 200 mg. of 7β-(3-hydroxy-6-methyl-2-pyridyl)thioacetamido-7α-methoxy-3-(1-methyltetrazol-5-yl)thiomethyl-Δ³-cephem-4-carboxylic acid.

Nuclear magnetic resonance spectra (D₆-DMSO)

δ(p.p.m.):

2.33 (3H, 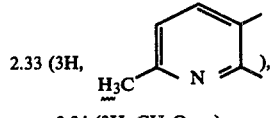), 3.34 (3H, CH₃O— ), about 3.87 (2H, —S—CH₂CO— ), 3.91 (3H, CH₃—N⟨ ), 5.08 (1H, 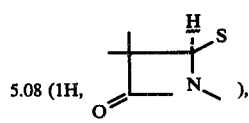), 6.82–6.98 (2H, 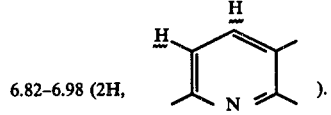).

What is claimed is:

1. The 7α-methoxy-7β-heterocyclic thioacetamido-3-heterocyclic thiomethyl-Δ³-cephem-4-carboxylic acid represented by the formula

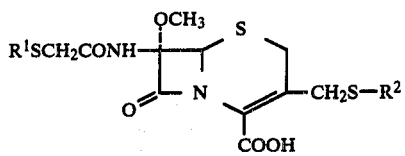

and the pharmaceutically acceptable salts thereof wherein R¹ is

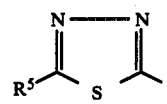

wherein R⁵ represents a hydroxy group, an amino group, a mercapto group, a lower alkylamino group having 1 to 4 carbon atoms, a lower alkanoylamino group having 1 to 4 carbon atoms, a lower alkoxycarbonylamino group having 1 to 4 carbon atoms in the alkoxy moiety, a carboxy lower alkylthio group having 1 to 4 carbon atoms in the alkyl moiety, or a 3-lower alkylureido group having 1 to 4 carbon atoms in the alkyl moiety; and R² is a 5-lower alkyl-1,3,4-thiadiazol-2-yl group.

2. The 7α-methoxy-7β-heterocyclic thioacetamido-3-heterocyclic thiomethyl-Δ³-cephem-4-carboxylic acid represented by the formula

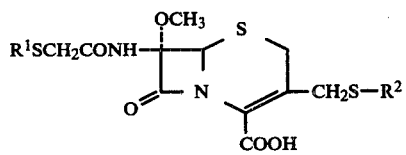

and the pharmaceutically acceptable salts thereof wherein R¹ is

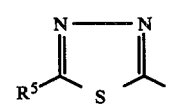

wherein R⁵ represents a hydroxy group, an amino group, a mercapto group, a lower alkylamino group having 1 to 4 carbon atoms, a lower alkanoylamino group having 1 to 4 carbon atoms, a lower alkoxycarbonylamino group having 1 to 4 carbon atoms in the alkoxy moiety, a carboxy lower alkylthio group having 1 to 4 carbon atoms in the alkyl moiety, or a 3-lower alkylureido group having 1 to 4 carbon atoms in the alkyl moiety; and R² is a 1-lower alkyl-tetrazol-5-yl group.

3. 7β-(5-Amino-1,3,4-thiadiazol-5-yl)thioacetamido-7α-methoxy-3-(1-methyltetrazol-5-yl)thiomethyl-Δ³-cephem-4-carboxylic acid.

* * * * *